United States Patent [19]
Woods et al.

[11] Patent Number: 5,359,101
[45] Date of Patent: Oct. 25, 1994

[54] ANIONICALLY POLYMERIZABLE MONOMERS, POLYMERS THEREOF AND USE OF SUCH POLYMERS IN PHOTORESISTS

[75] Inventors: John Woods, Dublin; Pauline Coakley, Kilkenny, both of Ireland

[73] Assignee: Loctite Ireland, Ltd., Dublin, Ireland

[21] Appl. No.: 769,511

[22] Filed: Oct. 1, 1991

Related U.S. Application Data

[63] Continuation of Ser. No. 542,464, Jun. 22, 1990, abandoned.

[30] Foreign Application Priority Data

Nov. 21, 1989 [IE] Ireland .................................. 3713/89

[51] Int. Cl.$^5$ .......................... C07F 7/28; C07F 7/10
[52] U.S. Cl. ..................................... 556/52; 556/55; 556/56; 556/415; 556/416; 556/417; 556/428; 556/432; 556/436; 556/437; 556/438; 556/439; 556/440; 556/441; 556/442; 526/298
[58] Field of Search ............... 556/415, 436, 438, 439, 556/442, 416, 417, 428, 432, 437, 440, 441, 52, 55, 56

[56] References Cited

U.S. PATENT DOCUMENTS

| | | | |
|---|---|---|---|
| 2,391,251 | 8/1941 | Long | 260/464 |
| 2,467,926 | 4/1949 | Ardis | 260/465.4 |
| 2,665,299 | 1/1954 | Ardis | 260/465.8 |

(List continued on next page.)

FOREIGN PATENT DOCUMENTS

| | | | |
|---|---|---|---|
| 48899A2 | 4/1982 | European Pat. Off. | |
| 84108095.5 | 4/1985 | European Pat. Off. | |
| 58-108213 | 6/1983 | Japan | |
| 58-123727 | 7/1983 | Japan | |
| 217376 | 9/1985 | Japan | |
| 060062 | 3/1986 | Japan | |
| 61-168607 | 7/1986 | Japan | C08F 230/08 |
| 62-77393 | 4/1987 | Japan | |
| 62-215595 | 9/1987 | Japan | |
| 64-56687 | 3/1989 | Japan | |
| 4-202195 | 7/1992 | Japan | |
| WO85/02030 | 5/1985 | PCT Int'l Appl. | |

OTHER PUBLICATIONS

Kadykov, V. V. and D. A. KochKin: Synthesis and Properties of Siloxane Cyanoacrylate Adhesives. *Plast. massy*, 1984, No. 10, pp. 8–9.

(List continued on next page.)

*Primary Examiner*—Mark Naguno
*Attorney, Agent, or Firm*—Vidas, Arrett & Steinkraus

[57] ABSTRACT

Anionically polymerizable monomers containing at least one silicon or titanium atom form polymeric photoresists having good dry etch resistance for use in microlithography. The monomers are of the formula $$A-CH=C\genfrac{}{}{0pt}{}{X}{Y} \qquad I$$

wherein A is —H or —CH=CH$_2$;
X is a strong electron withdrawing group;
Y is a strong electron withdrawing group containing at least one silicon or titanium atom.

Preferably Y is $$-COO(CH_2)_n-\underset{\underset{R^4}{|}}{\overset{\overset{R^3}{|}}{Si}}-R^2$$

wherein n is 1–5 and $R^2$, $R^3$ and $R^4$ are $C_1$–$C_{10}$ alkyl. A particularly preferred monomer is 3-trimethylsilylpropyl 2-cyanoacrylate.

Methods for applying a resist coating by vapor deposition of these monomers and exposure to radiation are described. A positive or negative tone image can be produced, depending upon the imaging method employed. The imaging layer may be applied over a planarizing layer to form a multilayer photoresist.

21 Claims, 2 Drawing Sheets

U.S. PATENT DOCUMENTS

| | | | |
|---|---|---|---|
| 2,721,858 | 10/1955 | Joyner et al. | 260/67 |
| 2,922,807 | 1/1960 | Merker | 260/448.2 |
| 2,985,682 | 5/1961 | Raffelson | 260/464 |
| 3,142,698 | 7/1964 | Halpren et al. | 260/465.4 |
| 3,254,111 | 5/1966 | Hawkins et al. | 260/465.4 |
| 3,316,227 | 4/1967 | Gerber | 260/88.7 |
| 3,355,482 | 11/1967 | Coover, Jr. et al. | 260/464 |
| 3,463,804 | 8/1969 | Ray et al. | 260/465 |
| 3,654,340 | 4/1972 | Banitt | 260/465.4 |
| 3,699,127 | 10/1972 | O'Sullivan et al. | 260/33.2 |
| 3,742,018 | 6/1973 | O'Sullivan | 260/465.4 |
| 4,012,402 | 3/1977 | Buck . | |
| 4,081,276 | 3/1978 | Crivello et al. . | |
| 4,153,641 | 5/1979 | Deichert et al. . | |
| 4,279,984 | 7/1981 | Matsuda et al. . | |
| 4,348,473 | 9/1982 | Okumura et al. . | |
| 4,425,471 | 1/1984 | Millet | 526/298 |
| 4,539,250 | 9/1985 | Fujii et al. . | |
| 4,551,418 | 11/1985 | Hult et al. | 430/325 |
| 4,675,270 | 6/1987 | Woods et al. | 430/311 |
| 4,675,273 | 6/1987 | Woods et al. | 430/325 |
| 4,810,766 | 3/1989 | Ohmari et al. . | |
| 4,965,387 | 10/1990 | Shinohara et al. | 556/440 |
| 5,187,048 | 2/1993 | Woods et al. | 430/286 |
| 5,200,238 | 4/1993 | McArdle et al. | 428/1 |

OTHER PUBLICATIONS

Abstract CA102(8):62883y "Synthesis and Properties of Siloxane, Cyanoacrylate Adhesive" By Kadykov V. V. and Kochkin D.A.

Kandor, I. I. et al. Chemical Properties of α–Cyanoacrylic Acid, *Zhurnal Obshchei Khimii*, 60, (1990), pp. 2160–2168.

N. Ono et al., *Bull. Chem. Soc. Jap.*, 51(8), 2401 (1978).

A. Polyakova et al., *Zh. Org. Khim.*, 3(7), 1205 (1967).

A. Said, *Chimica*, 28(5), 234 (1974).

V. Etlis et al., *Zh. Prikl. Khim.*, 44(4), 937 (1971).

Mukaiyama *Angew. Chem.* 18(10), 707 (1979).

Saigo et al., *Bull Chem. Soc. Jap.*, 50(7), 1863 (1977).

Mukaiyama et al., *Chem. Lett.*, 1975, 1045.

M. Feiser, *Feiser and Feiser's Reagents For Organic Synthesis*, 8, p. 95, John Wiley & Sons (1980).

WPI 80–82239C/46, Abstracting Su 726086 (1980).

G. H. Millet in *Structural Adhesives*, (Hartshorn, Ed.), p. 261, Plenum Press, (1986).

Y. Tanaka et al. in *Epoxy Resins, Chemistry and Technology*, (C. May Ed.), p. 333, Marcel Decker (1988).

L. J. Bellamy, *The Infra–Red Spectra of Complex Molecules*, pp. 263–265, Methuen & Co. (1954).

C. Colby in *Cyanoacrylate Resins–The Instant Adhesives*, (H. Lee Ed.), p. 25, Pasadena Technology Press (1981).

Translation of DE 34 15 181 (10/85).

USPTO Translation of JP 64–56687.

CA 97(4): 31279E.

CA 99(22):185932r.

Polymer Preprints Japan (English Edition), vol. 39, No. 1, III–4–13 (1990).

A. Reiser, in "Photo Reactive Polymers" Wiley 1989, 359–393, especially 375–381.

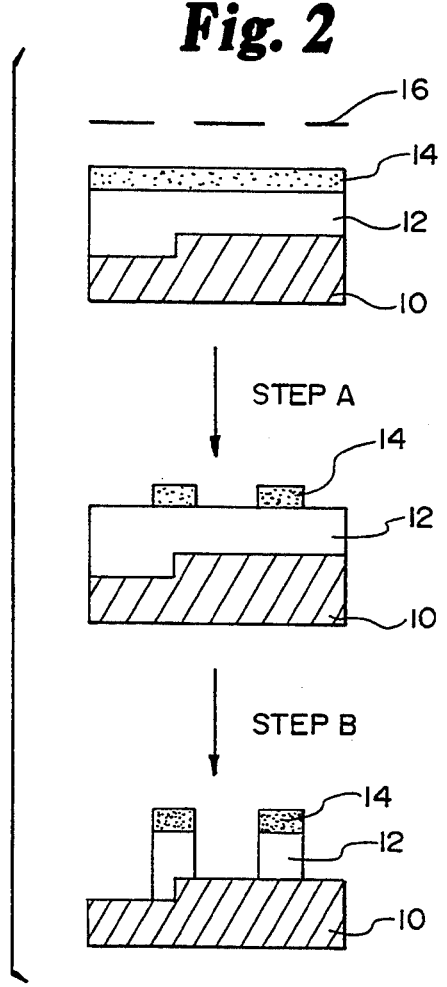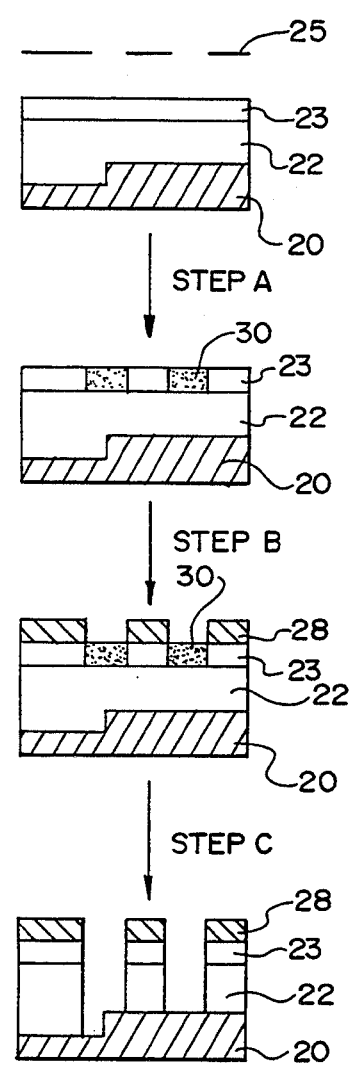

ANIONICALLY POLYMERIZABLE MONOMERS, POLYMERS THEREOF AND USE OF SUCH POLYMERS IN PHOTORESISTS

This is a continuation of copending application(s) Ser. No. 07/542,464 filed on Jun. 22, 1990 now abandoned.

CROSS REFERENCE TO RELATED APPLICATIONS

This Application is related to application Ser. No. 07/542,465, now abandoned, entitled "Photoresists formed by Polymerization of Di-Unsaturated Monomers" filed on even date herewith claiming priority from Irish Patent Application No. 2044/89, now abandoned, a division of which has now issued as U.S. Pat. No. 5,200,238, incorporated herein by reference, and application Ser. No. 07/542,466 now abandoned, entitled "Liquid Crystal Display Devices" filed on even date herewith, now abandoned, incorporated herein by reference, a continuation-in-part of which has now issued as U.S. Pat. No. 5,187,048.

BACKGROUND OF THE INVENTION

1. Field of the Invention

This invention relates to anionically polymerizable monomers containing at least one silicon or titanium atom, polymers thereof, and use of such polymers in photoresists, particularly for the microelectronics industry. In one aspect this invention also relates to vapour deposition and polymerization of silicon-functionalised cyanoacrylates.

2. Description of the Related Art

The use of anionically (or zwitterionically) polymerisable monomers as resist materials for microlithography is known in the art, as discussed in U.S. Pat. Nos. 4,675,273 Woods et al. and 4,675,270 Woods et. al. both assigned to Loctite (Ireland) Limited, the contents of which are incorporated herein by reference. Such resist materials are usually applied to or formed as a coating on an etchable substrate; the coated substrate is then imaged using high energy radiation; the image is developed by a development process, normally using a solvent; and the image is etched using a suitable plasma or chemical etching process.

Chemical etching has a significant disadvantage in that it is isotropic, i.e. the etching can affect the substrate below the photoresist. To achieve anisotropic etching, it is preferred to use dry etching by radio frequency glow discharge or large area ion beam methods. The most preferred methods are:

(i) plasma etching, e.g. using oxygen or a halocarbon, particularly a fluorocarbon such as $CF_4$ or $CH_2F_2$ with chlorine or argon; or (ii) reactive ion etching.

(See "Plasma Etching" by J. A. Mucha and D. W. Hess in "Introduction to Microlithography"(L. F. Thompson, C. G. Willson and M. J. Bowden Ed.) ACS Symposium Series 219, Am. Chem. Soc. (1983), 216–285; and "Multilayer Techniques and Plasma Processing" by A. Reiser in "Photoreactive Polymers—the Science and Technology of Resins", John Wiley & Sons (1989), 359–393).

However in plasma etching the photoresist itself is vulnerable to being etched away. There is a need therefore for polymeric photoresist films which have a good dry etch resistance. It is known to increase the plasma resistance of a resist material by including silicon in it (see the Reiser reference mentioned above, pages 375–381). U.S. Pat. No. 4,551,418 Hult et. al. describes a process for generating a negative tone resist image comprising the steps of:

(1) coating a substrate with a film that contains a cationic photoinitiator;

(2) exposing the film in an imagewise fashion to radiation and thereby generating cationic initiator in the exposed regions of the film;

(3) treating the exposed film with a cationic sensitive monomer to form a film of polymer resistant to plasma etching; and (4) developing the resist image by etching with a plasma.

The cationic sensitive monomer may be an organometallic monomer wherein the organometallic elements include silicon, germanium and tin. Particular examples of monomers include an epoxy substituted siloxane or silane or a silyl substituted vinyl ether. The monomer may be dissolved in a solvent or may be in the vapor state.

However there is no teaching concerning improving the dry etch resistance of anionically polymerizable resist materials.

SUMMARY OF THE INVENTION

The present invention provides anionically polymerizable monomers of the formula I

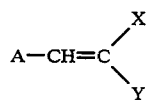

wherein A is —H or —CH=$CH_2$;

X is a strong electron withdrawing group;

Y is a strong electron withdrawing group containing at least one silicon or titanium atom.

The term "strong electron withdrawing group" refers to groups which are more electron withdrawing than halo.

X may suitably be selected from —CN, —COR, —COOR, —$SO_2R$ and —$SO_3R$ wherein R is H or a hydrocarbyl group preferably a $C_1$-$C_{12}$ hydrocarbyl group. Preferably X is —CN.

Y may suitably be selected from —$COR^1$, —$COOR^1$, $SO_2R_1$ and —$SO_3R^1$ wherein $R^1$ is a group containing Si or Ti, preferably a hydrocarbyl, aryl or hydrocarbylaryl group (or a substituted derivative thereof) substituted with a group containing Si or Ti.

The term "hydrocarbyl" as used herein means "aliphatic hydrocarbyl" including alkyl, alkenyl and alkynyl. Hydrocarbyl groups shall preferably contain from 1 to 10 carbon atoms, more preferably from 1 to 5 carbon atoms, and aryl and hydrocarbylaryl groups shall preferably have from 6 to 20 carbon atoms, more preferably from 6 to 10 carbon atoms. Hydrocarbyl groups are preferred, especially alkyl or alkenyl groups. A substituted derivative of the foregoing may suitably be substituted with one or more halo or alkoxy groups or interrupted by one or more oxygen or nitrogen atoms. Halogen may be chlorine, bromine, fluorine or iodine.

Specific examples of the groups for $R^1$ are a methyl group, an ethyl group, an n-propyl group, an isopropyl group, an n-butyl group, an isobutyl group, a pentyl group, a hexyl group, an allyl group, a methallyl group, a crotyl group, a propargyl group, a cyclohexyl group, a benzyl group, a phenyl group, a phenoxide group, a cresyl group, a 2-phenylethyl group, a 2-chloroethyl group, a 3-chloropropyl group, a 2-chlorobutyl group, a trifluoroethyl group, a 2-methoxyethyl group, a 3-methoxybutyl group or a 2-ethoxyethyl group, substituted with a group containing Si or Ti.

Preferably $R^1$ comprises or is substituted with at least one group consisting of or containing

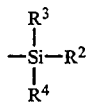

wherein $R^2$, $R^3$ and $R^4$ which may be the same or different are selected from H (provided that not more than one of $R^2$, $R^3$ and $R^4$ is H), $C_1$–$C_{10}$ alkyl, aryl , $C_1$–$C_{10}$ alkoxy and siloxy groups of the formula:

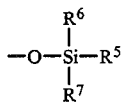

wherein $R^5$, $R^6$ and $R^7$ which may be the same or different are selected from H, $CH_3$ or phenyl provided that not more than one of $R^5$, $R^6$ and $R^7$ is H;
and wherein $R^2$ may also be a group selected from siloxane oligomers or polymers of the structure

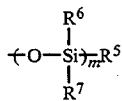

wherein $R^5$, $R^6$ and $R^7$ are defined as above and m is an integer from 2 to 100.

Preferably m is in the range from 2 to 20, and most preferably in the range from 2 to 5. In the case of monomers intended for vapour deposition it is desirable that m be low, for example not more than 2.

TABLE I $$A-CH=\underset{\underset{O}{\|}}{\overset{\overset{CN}{|}}{C}}-C-O-R$$

| A | R | No. |
|---|---|---|
| H— | ⌬–Si(CH₃)₃ (para) | 1. |
| H— | ⌬–Si(CH₃)₃ (meta) | 2. |
| CH₂=CH— | ⌬–Si(CH₃)₃ (meta) | 3. |
| H— | 3,5-(Si(CH₃)₃)₂-phenyl | 4. |
| H— | ⌬–CH₂Si(CH₃)₃ (para) | 5. |
| CH₂=CH— | ⌬–O–Si(CH₃)₃ (para) | 6. |
| H— | ⌬–O–Si(CH₃)₃ (meta) | 7. |
| CH₂=CH— | –CH₂–⌬–Si(CH₃)₃ (para) | 8. |
| H— | –CH₂CH₂–⌬–Si(CH₃)₃ (meta) | 9. |
| H— | –CH₂–C≡C–Si(CH₃)₃ | 10. |
| CH₂=CH— | –CH(CH₃)–C(=CH₂)–Si(CH₃)₃ | 11. |
| CH₂=CH— | –Si(CH₃)₃ | 12. |
| H— | –Si(CH₃)₂–phenyl | 13. |
| H— | –Si(CH₃)₂–CH(CH₃)₂ | 14. |
| H— | –CH₂–Si(CH₃)₃ | 15. |
| CH₂=CH— | –CH₂–Si(CH₃)(phenyl)– | 16. |
| H— | –(CH₂)₃–Si(CH₃)₂–O–Si(CH₃)₃ | 17. |

Alkyl groups shall preferably contain 1 to 5 carbon atoms and aryl groups shall preferably have from 6 to 10 carbon atoms, most preferably being phenyl.

More preferably Y is

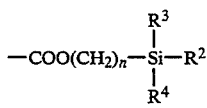

where n is 1–5 and $R^2$, $R^3$ and $R^4$ are as defined above. Preferably n is at least 3. Preferably $R^2$, $R^3$ and $R^4$ are $C_1$–$C_{10}$ alkyl.

A particularly preferred monomer is 3-trimethylsilylpropyl 2-cyanoacrylate of the formula II

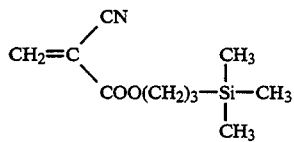

Other examples of the monomers are the following monomers Nos. 1–17 whose formulae are set out in Table 1 below:

| No. | MONOMER |
| --- | --- |
| 1. | 4'-Trimethylsilylphenyl 2-cyanoacrylate |
| 2. | 3'-Trimethylsilylphenyl 2-cyanoacrylate |
| 3. | 3'-Trimethylsilylphenyl 2-cyanopenta-2,4-dienoate |
| 4. | 3',5'-Bis (Trimethylsilyl)phenyl 2-cyanoacrylate |
| 5. | 4'-(Trimethylsilylmethyl)phenyl 2-cyanoacrylate |
| 6. | 4'-Trimethylsilyloxphenyl 2-cyanopenta-2,4-dienoate |
| 7. | 3'-(Trimethylsilylmethyloxy)phenyl 2-cyanoacrylate |
| 8. | 4'-Trimethylsilylbenzyl 2-cyanopenta-2,4-dienoate |
| 9. | 2,(3''-Trimethylsilylphenyl)ethyl 2-cyanoacrylate |
| 10. | 1'-Trimethylsilylpropargyl 2-cyanoacrylate |
| 11. | 3'-Methyl-2'-Trimethylsilylallyl 2-cyanopenta-2,4-dienoate |
| 12. | Trimethylsilyl 2-cyanopenta-2,4-Dienoate |
| 13. | Phenyldimethylsilyl 2-cyanoacrylate |
| 14. | Dimethylisopropylsilyl 2-cyanoacrylate |
| 15. | Trimethylsilylmethyl 2-cyanoacrylate |
| 16. | Phenyldimethylsilylmethyl 2-cyanopenta-2,4-dienoate |
| 17. | 3-Pentamethyldisiloxypropyl 2-cyanoacrylate |

The monomers wherein A is $-CH=CH_2$ may be prepared by methods analogous to those described in our co-pending application Ser. No. 07/542,465, now abandoned entitled "Photoresists formed by Polymerization of Di-Unsaturated Polymers" claiming priority from Irish Patent Application No. 2044/89 e.g. by reaction of acrolein with an appropriately substituted alkyl cyanoacetate.

The present invention also provides polymers formed by anionic polymerization of monomers of Formula I as described above. In particular the invention provides polymeric photoresists formed by polymerisation of monomers of Formula I. The photoresists are preferably formed by polymerization from monomer vapour to produce a polymeric film on a substrate, in the manner described in U.S. Pat. Nos. 4,675,273 or 4,675,270. In one aspect therefore, the invention provides a method for applying a polymeric resist coating to a substrate which comprises exposing the substrate to the vapour of a monomer of formula I as defined in claim 1 for sufficient time to deposit a polymerized coating of the monomer on the substrate. In a further aspect, the substrate has a planarizing layer of etchable polymeric material applied thereto before the resist coating of the monomer of formula I is deposited thereon.

Alternatively the monomer may be polymerized in solution or in the bulk state and deposited on the substrate e.g. by spin coating to form a photoresist.

Photoresist films produced from monomers of Formula I may be processed similarly to conventional polycyanoacrylates, but they have significantly improved dry etch resistance as compared to photoresists formed of conventional polycyanoacrylates. They also have improved dry etch resistance as compared to other conventional photoresist materials exemplified by poly(methylmethacrylate) and Novolac systems.

Photoresist films produced from monomers of Formula I have been found to normally image with negative tone, in contrast with photoresists formed from conventional poly(cyanoacrylates) which image with positive tone. By "negative tone" is meant that upon exposure to UV radiation through a mask followed by solvent treatment, the unexposed areas are dissolved away, whereas by "positive tone" is meant that on similar treatment the exposed areas are removed by the solvent.

Alternatively the monomers of Formula I may be used to form photoresists with positive tone images by coating the substrate with a compound which releases acid upon irradiation, image-wise exposing the coated substrate, and then forming the photoresist by deposition from monomer vapour, as described in U.S. Pat. No. 4,675,270 for poly(cyanoacrylates).

In the case of deposition from solution, a polymer is prepared and then dissolved in a suitable solvent such as dichloromethane, acetone, nitromethane, tetrahydrofuran, acetonitrile, or chloroform. In the case of vapour deposition processes, the monomer vapours may be generated from the monomers at ambient temperatures and pressures but it is generally preferred to heat the monomers and/or reduce the atmospheric pressure above the monomer generated in the chamber in order to generate sufficient concentrations of vapour to accomplish the polymer deposition on the substrate in a reasonable time.

Virtually any substrate upon which a polymeric image is desired may be utilized in the inventive processes. Most advantageously, the substrates will be ones which undergo subsequent plasma etching during which the polymer coating serves as an etch resist. Suitable substrate materials include silicon dioxide, including $SiO_2$ coated silicon, metallic oxides, and glass, all of which may be etched by plasma etching processes.

The preferred substrate is $SiO_2$ coated silicon, e.g. the silicon chips conventionally used in preparation of semiconductor devices. Most suitably, this substrate is etched by plasma etching process.

If desired, more particularly where the substrate has a stepped surface, a planarizing layer of etchable polymeric material such as poly(methylmethacrylate) may be applied to the substrate before the resist layer is applied thereon.

the case of vapour deposition processes, no surface treatment will be necessary if the substrate surface is inherently active for inducing anionic or zwitterionic polymerization of the monomer. In certain cases, however, where the substrate is slightly acidic or neutral it is necessary to activate the surface with a basic liquid or vapour which is substantially removed before exposing the substrate to the monomer vapour. Suitable activators include the known initiators for anionic or zwitterionic polymerization of alkyl cyanoacrylates. Especially suitable activators are organic amines and phosphines.

A conventional solvent development process may be used to develop the image, e.g. immersion in ethyl acetate, isobutyl methyl ketone, acetone or blends of ethyl acetate with either of isobutyl methyl ketone and acetone. Compounds which release acid upon irradiation for the process of forming a positive tone photoresist include any compounds which release Lewis or protonic acids such as those known as photoinitiators for cationically polymerizable resins such as epoxies or vinyl ethers.

Additionally included are compounds which release sulfonic acids upon irradiation and are known as photolytically releasable latent thermal catalysts for acid curable storing lacquers.

Suitable radiation sensitive acid precursors useful in the inventive method include salts of complex halogenides represented by the formula $$[A]_d{}^+[MX_e]^{-(e-f)}$$

wherein A is a cation selected from iodonium, iodosyl, Group VIa onium, pyrylium, thiopyrylium, sulfonylsulfoxonium, and diazonium, M is a metal or metalloid, X is a halogen radical, d=e-f, f=the valence of M and is an integer equal to from 2 to 7 inclusive and e is greater than f and is an integer having a value up to 8; compounds of the formula $$R^8[O.SO_2-CQ_3]_{n'}$$

wherein $R^8$ is an organic radical of valency 1 to 4 and Q is hydrogen or fluorine and n' is an integer from 1 to 4; and compounds which release sulfonic acids when irradiated such as those disclosed in U.S. Pat. Nos. 4,504,372 and 4,510,290, both incorporated herein by reference.

The acid generating compound may be applied neat or in a solvent which is subsequently evaporated. If a surface activator is also to be applied to the substrate, both the activator and the acid generating compound may be applied simultaneously in a common solvent. Alternatively, the activator may be applied before or after application of the acid generating compound.

Only trace amounts of surface activator and acid generating compound are necessary. Mirror finish substrates may be repolished, e.g. with a suitable tissue, after application of these compounds and still retain sufficient activator and acid generator to give sharply imaged resists after irradiation and exposure to monomer vapour.

BRIEF DESCRIPTION OF THE DRAWINGS

Embodiments of the invention are described below in the Examples and with reference to the accompanying drawings in which:

FIG. 2 is a schematic diagram of the negative imaging methodology for a multilayer photoresist system, FIG. 3 is a schematic diagram of selective deposition of monomer on an inhibitor-imaged substrate,

DESCRIPTION OF THE PREFERRED EMBODIMENTS

EXAMPLE 1

Preparation of 3-trimethylsilylpropyl cyanoacetate

Figure 1:
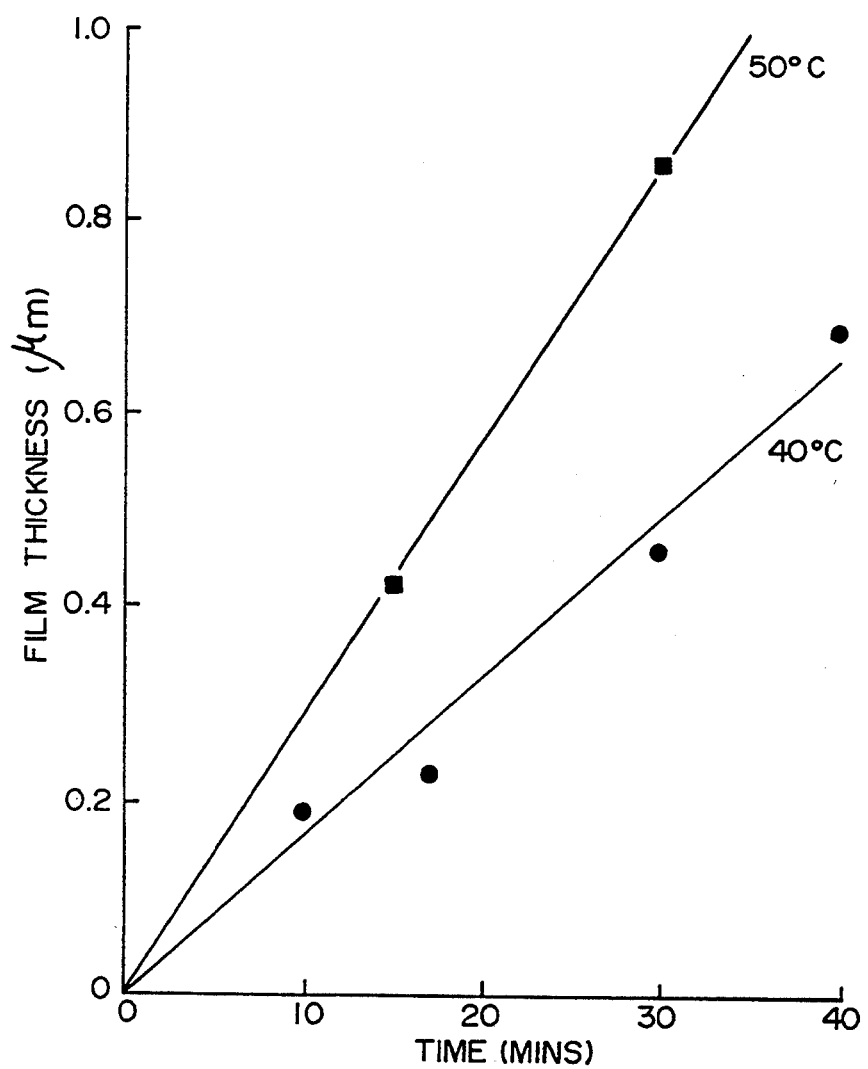
FIG. 1 is a graph showing vapour deposition growth rates of 3-trimethylsilylpropyl 2-cyanoacrylate as described in Example 3.

Cyanoacetic acid (14.20 g, 0.167 moles), 3-trimethylsilylpropan-1-ol (22.04 g, 0.167 moles) and p-toluenesulfonic acid monohydrate (0.18g) were dissolved in toluene (100 mls) and heated under reflux in a Dean Stark apparatus until the quantitative amount of expected water from esterification (3.09) was recovered. The reaction mixture was cooled and allowed to stand at room temperature for four days during which time small quantity of a white crystalline solid separated. The mixture was filtered to remove the solid material and the solvent removed from the filtrate by distillation under reduced pressure. This process yielded a clear, colourless, low viscosity liquid in quantitative yield (34 g) which was shown by $^1$Hnmr and I.R. analyses to be 3-trimethylsilylpropyl cyanoacetate of the structure:

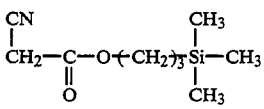

$^1$Hnmr, 60 mHz (CDCl$_3$):
 τ10.0 singlet, 9H, (CH$_3$)$_3$—Si
 τ9.6, multiplet, 2H, —CH$_2$—Si
 τ8.4, multiplet, 2H, —CH$_2$—
 τ6.7, singlet, 2H, —CH$_2$—CN
 τ5.9, triplet, 2H, O—CH$_2$—
I.R. (NaCl, film):
 2950 cm$^{-1}$, C–H stretching vibration
 2250 cm$^{-1}$, C≡N stretching vibration
 1750 cm$^{-1}$, C═O stretching vibration
 1250 cm$^{-1}$, Si—CH$_3$ symmetric deformating vibration

EXAMPLE 2

Preparation of 3-Trimethylsilylpropyl 2-cyanoacrylate 3-trimethylsilylpropyl 2-cyanoacetate (31.84 g, 0.16 moles) prepared as described in Example 1, was added dropwise over 10 minutes to a stirred solution of paraformaldehyde (4.8 g, 0.16 moles formaldehyde) and piperidine (0.12 g) in n-butylacetate at 70° C. The mixture was heated under reflux in a Dean-Stark apparatus until the quantitative amount of water expected from formaldehyde condensation had been collected (2.8 g). The mixture was allowed to cool and phosphorous pentoxide (0.57 g), p-toluenesulfonic acid (1.09 g) and 1,4-hydroquinone (2.18g) were added. The solvent was removed by distillation under reduced pressure to yield a viscous, orange/yellow coloured liquid. The liquid was fractionated under reduced pressure to give crude monomer (16.80 g b.p. 150°–180° C. at 0.7–10 mbar). Vacuum distillation of the crude material onto a catalytic quantity of methanesulfonic acid and 1,4-hydroquinone (10$^{-4}$g) afforded the pure product 3-trimethylsilylpropyl 2-cyanoacrylate as a slightly yellow coloured reactive liquid (12.45 g, 37%).

Spectral analysis confirmed the structure of the product to be:

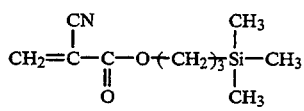

¹Hmr, 60MH$_z$(CDCl$_3$),
τ10.0, singlet, 9H, Si—(CH$_3$)$_3$
τ9.5, multiplet, 2H, —CH$_2$—Si
τ8.3, multiplet, 2H, —CH$_2$—
τ5.8, triplet, 2H, O—CH$_2$—
τ3.2, doublet, 2H, CH$_2$=C, J$_{H-H}$=25H$_z$
I.R. (NaCl, film)
2950 cm$^{-1}$ —C—H stretching vibration
2230 cm$^{-1}$ —C≡N stretching vibration
1740 cm$^{-1}$

stretching vibration
1615 cm$^{-1}$ C=C conjugated, stretching vibration

EXAMPLE 3

Vapour Deposition & Polymerization of 3-trimethylsilylpropyl 2-cyanoacrylate

Photoresist layers of poly(3-trimethylsilylpropyl 2-cyanoacrylate) were prepared by a vapour phase deposition process of the corresponding monomer, prepared as described in Example 2, according to the following procedure. A polished silicon wafer three inches in diameter was activated by pouring a sufficient quantity of a solution of 10% N, N, N, N-tetramethylethylenediamine (TMED) in 1,1,1,3,3,3-hexamethyldisilazane (HMDS) to cover the surface. The wafer was then spun at 4,000 rpm to restore the mirror finish and mounted in the top of closed cylindrical chamber 11 cm. in diameter consisting of an aluminium base and plastic sides 2 cm in height into which 2.0 grams of monomer 3-trimethylsilylpropyl 2-cyanoacrylate had been placed. The chamber was mounted on thermostatically controlled hot plate and preheated to 40° C. prior to the introduction of the activated wafer. The wafer was mounted such that the treated polished side was located 2 cm directly above the heated monomer liquid and in contact with its vapour. A thin polymer film was formed on the silicon wafer during its exposure to the vapour.

The process was repeated for different periods of exposure to monomer vapour and it was found that the amount of material deposited and hence the film thickness was directly related to the vapour exposure as the following data indicates:

| Wafer Sample No. | Vapour Exposure Time (mins) | Weight of Resist Film (mg) | Calculated Film Thickness (μm) |
|---|---|---|---|
| 1 | 10 | 0.86 | 0.19 |
| 2 | 17 | 1.04 | 0.23 |
| 3 | 30 | 2.11 | 0.46 |
| 4 | 40 | 3.14 | 0.69 |

Assuming a density of 1 g.cm$^{-3}$ for the polymer film, the corresponding film thickness may be calculated according to the relationship:

$$d = \frac{1000\,m}{\pi r^2}$$

where
d = film thickness in μm
m = mass of deposited polymer in mg
r = radius of the silicon substrate in mm The process was repeated with the monomer temperature adjusted to 50° C. In this case, it was also found that the quantity of polymer deposited was directly related to the period of vapour exposure but the rate of deposition was greater at the higher temperature. The results at 50° C. were as follows:

| Wafer Sample No. | Vapour Exposure Time (Mins) | Weight of Resist Film (Mg.) | Calculated Film Thickness (μm) |
|---|---|---|---|
| 5 | 15 | 1.90 | 0.42 |
| 6 | 30 | 3.92 | 0.86 |

By plotting the vapour exposure time against the calculated film thickness the polymer deposition growth rates were found (from the slopes of the lines) to be 0.017 and 0.029 μm min$^{-1}$ for 40° and 50° C. respectively (cf. FIG. 1).

EXAMPLE 4

Ultraviolet Light Lithographic Evaluation of Poly(3-methylsilylpropyl 2-cyanoacrylate) resist A silicon wafer, 3 inches in diameter was vapour coated with 2.1 milligrams (0.46 μm) of poly (3-trimethylsilylpropyl 2-cyanoacrylate) by the procedure described in Example 3. The coated wafer was then imagewise exposed to ultraviolet (UV) light from a medium pressure mercury arc lamp (operating at 80 Wcm$^{-1}$) through a 4 inch (10 cm) square chrom plated quartz test mask which had alternate opaque and transmissive elements of varying sizes over the range 1000–1 micrometers patterned on the surface. To ensure adequate contact between the mask and coated wafer, a copper plate 4 inches (10 cm) square and ⅝ inches (1.6 cm) in thickness with a 2 inch (5 cm) square centralized hole was placed on the perimeter of the mask. The weight of the copper plate was 1 kilogram. The coated wafer, mask and copper plate assembly was located directly below the arc lamp such that the distance between the arc and wafer was 20 cms. The wafer was exposed to UV light for 120 seconds, cooled to room temperature and immersed for 30 secs. in a bath of developer solvent, prepared by blending one part of toluene with 4 parts of petroleum spirit b.p. 40°–60° C. During this period, a negative tone relief image of the mask pattern had formed in the resist layer. A microscopic examination of the imaged wafer showed minimum feature sizes of 2.5 μm. In all cases unexposed resist was cleanly removed by the developer solvent.

EXAMPLE 5

Electron Beam Lithographic Evaluation of Poly(3-trimethylsilylpropyl 2-cycanoacrylate) resist A silicon wafer, 3 inches in diameter was vapour coated with 3.55 milligrams (0.78 μm) of poly(3-trimethylsilylpropyl 2-cyanoacrylate) by the method described in Example 3. The coated wafer was scribed and broken in small pieces approximately 10×10 mm$^2$ in size. The small wafers were mounted in a scanning electron microscope and exposed to an electron beam, 0.1 μm in diameter, at an accelerating voltage of 25 KV for varying current beam densities (radiation dose) over the range 41-205 μC.cm$^{-2}$. A series of 8 lines 10, 5, 2, 1, 0.8, 0.6, 0.4 and 0.3 μm were irradiated in a vector scan mode. Following irradiation, the wafers were developed by immersion in a bath of a toluene/petroleum spirit blend (4:96) for 60 secs. followed by rinsing with isopropyl alcohol for 60 secs.

In all cases where imaging occurred, a negative tone was observed which indicates that the solubility of the resist decreases on exposure to electron beams. This may be indicative of an electron beam induced cross-linking reaction. The results obtained were as follows:

| Sample No | Current Beam Density (μC.cm$^{-2}$) | Developed Lines (μm) |
|---|---|---|
| 7-1 | 41 | None |
| 7-2 | 82 | None |
| 7-3 | 123 | 10 and 5 |
| 7-4 | 164 | 10,5 and 2 |
| 7-5 | 205 | 10,5 and 2 |

In all cases, the development solvent removed all resist not exposed to the electron beam.

EXAMPLE 6

Evaluation of the Plasma Etch Resistance of Poly(3-trimethysilylpropyl 2-cyanoacrylate)

A silicon wafer approximately 1 cm$^2$ was vapour coated with 0.8 um of poly (3-trimethylsilylpropyl 2-cyanoacrylate) (PTSCA) according to the procedure described in Examples 3 and 5. The resist coated wafer was placed in a plasma reactor along with a similar substrate which had been sputter coated with 1.0 μm of silicon dioxide (SiO$_2$) and exposed to a plasma of argon and trifluoromethane (Ar/CHF$_3$) under reactive ion etching conditions at 120 watts for sufficient time to allow the etching rates to be determined. For comparative purposes, a similar substrate was vapour coated with 1.2 μm of poly(ethyl 2-cyanoacrylate) (PECA) and the plasma etching rate of this resist relative to SiO$_2$ was also measured under similar conditions. The results obtained were as follows:

| Resist | Resist Etch Rate Å.min$^{-1}$ | SiO$_2$ Etch Rate, Å.min$^{-1}$ | Resist/SiO$_2$ Etch Rate Ratio |
|---|---|---|---|
| PTSCA | 106 | 312 | 0.34 |
| PECA | 180 | 292 | 0.62 |

These results demonstrate a significant improvement in the etch resistance of the silicon containing cyanoacrylate resist compared to a similar photoresist which does not contain silicon.

The etch rate of PTSCA resist in an oxygen plasma was also determined in a related experiment. In this case, the etch resistance was compared not only to PECA but also to a number of commercially available photoresist products. The results obtained are as follows:

| Resist | Etch Rate, O$_2$ Plasma, Å.min$^{-1}$ | Relative Etch Resistance to PECA |
|---|---|---|
| PTSCA | 162 | 30.09 |
| PECA | 5000 | 1 |
| AZ 4330 (Hoechst) | 2814 | 1.8 |
| Microposit 2400 (Shipley) | 2172 | 2.3 |
| Photoresist 1400-27 (Shipley) | 2437 | 2.1 |

The experiment shows that the silicon containing PTSCA is over 30 times more resistant to O$_2$ plasma than non silicon containing PECA resist and approximately 15 times more resistant to a number of popular commercial products, Poly(3-Trimethylsilylpropyl 2-cyanoacrylate) as contact mask for Plasma and Deep Ultra Violet (DUV) Imaging of Planarizing Layers in Multilayer Photoresists (FIG. 2)

Examples 4–6 demonstrate the utility of the new polymer as a solvent developed, negative acting, single layer photoresist having outstanding resistance to plasma etching. The polymer is, however, also suitable as an imaging mask layer in a multilayer photoresist system. Multilayer resists are usually designed to separate the imaging function of a photoresist from its planarizing function and the technique is particularly useful where relief images over stepped features are required. A typical multilayer photoresist consists of an underlying relatively thick (1–5 μm) planarizing layer over which a thin imaging layer (0.1–0.3 μm) is deposited. The polymeric materials of the present development are particularly suitable for use as the thin imaging layer of multilayer resist system and function as a plasma or DUV contact mask ensuring image transfer through the planarizing layer to the substrate surface. This process is shown schematically in FIG. 2.

Referring to FIG. 2, the first step involves the application to a substrate 10 of a relatively thick planarizing layer 12 which may consist of any O$_2$ plasma or DUV sensitive polymeric material such as poly(methylmethacrylate) (PMMA). The polymer is applied by conventional means for example by spin casting from solution onto a substrate and baking to remove solvent. The polymeric solution may optionally contain a small quantity of a non-volatile anionic polymerization initiator such as an amine or phosphine (e.g. 0.01% piperonylamine). Alternatively, the surface of the dry polymer may be activated by a short exposure to vapour of a volatile amine (e.g. 2 mins. exposure to a solution of 50% hexamethyldisilazane in triethylamine). The planarizing layer 12 is next exposed to monomer 3-trimethylsilylpropyl 2-cyanoacrylate and the imaging layer 14 is grown (typically 0.1–0.3 μm film thickness). The preferred method of growth is by the vapour deposition procedure as outlined in Example 3 although the polymer may also be grown by immersion of the substrate in a solution of the monomer dissolved in a suitable solvent (e.g. two minutes immersion in 5% solution in petroleum spirit) or by spin casting from solution.

The bi-layer photoresist is then imagewise exposed to UV light through a mask 16 and the image developed as described in Example 4 (FIG. 2, step A). The photoresist is then exposed to an oxygen plasma for sufficient time to etch the planarizing layer and expose the substrate (FIG. 2, step B). Since the plasma etches anisotropically, relief images with excellent aspect ratios are achieved particularly over stepped features. Alternatively to plasma imaging, the imaged hi-layer resist may be flood exposed to DUV irradiation and the planarizing layer developed by means of a suitable solvent. The process described here may be modified to include the deposition of an isolation layer to prevent intermixing of the planarizing and imaging layer or the deposition of a DUV dye layer between the planarizing and imaging layer to enhance the contrast and resolution of the photo resist.

Process for Preparing Positive Relief Images of Poly (3-trimethylsilylpropyl 2-cyanoacrylate) (FIG. 3)

The lithographic examples relating to the above polymer so far described have been concerned only with the generation of negative tone images. It is however possible to provide positive tone images based on the above resist provided that the imaging step is carried out prior to deposition of the polymer.

This process, illustrated schematically in FIG. 3, is achieved by first coating a layer 23 of a photosensitive latent acid catalyst (i.e. a material capable of producing strong acid on exposure to radiation) over the substrate 20. This coating may preferably be a modified planarizing layer (e.g. 4 μm PMMA) or alternatively may be placed directly over a planarising layer 22. In the latter case, the layer 23 is conveniently referred to as an inhibitor layer (e.g. 0.2 μm film of poly (4-methoxystyrene) containing 20% by weight of CE 1014, a commercially available latent acid catalyst supplied by General Electric Corp. ). The layer(s) 22, 23 are deposited by conventional spin coating methods and preferably contain a small quantity of cyanoacrylate polymerization initiator. Useful latent acid catalysts include triarylsulfonium and diaryliodonium salts containing non-nucleophilic counterions and benzene sulfonate esters of benzoin and should account for between one and 30% of the dry polymer weight. Irradiation of the layer(s) 22, 23 through a mask 25 at wavelengths corresponding to the absorption characteristics of the latent acid, produces a pattern of strong acid in the inhibitor layer which corresponds to a positive image of the mask pattern (FIG. 3, Step A).

The patterned resist is next exposed to monomer 3-trimethylsilylpropyl 2-cyanoacrylate, preferably by vapour deposition as described in Example 3 although solution methods may also be used to selectively grow the corresponding polymer 28 on the unexposed regions of the inhibitor or photosensitive layer (FIG. 3, Step B)

Polymer 28 does not grow on the exposed areas 30 where the photogenerated strong acid inhibits the anionic polymerization of the monomer. It is important to ensure that concentration of photogenerated acid exceeds the concentration of anionic polymerization initiator included in the planarization or inhibitor layers. Thus a positive tone relief image of the mask is transferred into the photosensitive/inhibitor layer without the need for a solvent development step.

The imaged resist is next exposed to an oxygen plasma for sufficient time to transfer the image through the photosensitive/inhibitor and planarizing layer (if present) to expose the substrate (FIG. 3, Step C). This step may be preceded by flood exposing the coated wafer to DUV light to alter the solution characteristics of the plasma mask.

Alternatively, the image may be transferred by first flood exposure to DUV light and developing the image in a suitable solvent. The process is shown schematically in FIG. 3.

We claim:

1. Anionically polymerizable monomers of the formula I:

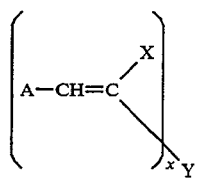

wherein A is —H or —CH=CH$_2$;

X is a strong electron withdrawing group selected from the group consisting of —CN, —COR, —COOR, —SO$_2$R and —SO$_3$R, wherein R is H or a hydrocarbyl group;

Y is a x-valent strong electron withdrawing group containing at least one silicon or titanium atom; and x is equal to 1.

2. Monomers according to claim 1 wherein Y is selected from —COR$^1$, —COOR$^1$, —SO$_2$R$^1$ and —SO$_3$R$^1$, wherein R$^1$ is a group containing Si or Ti.

3. Monomers according to claim 2 wherein R$^1$ is —Si(R$^2$)(R$^3$)(R$^4$), wherein R$^2$, R$^3$ and R$^4$, which may be the same or different are selected from H (provided that not more than one of R$^2$, R$^3$ and R$^4$ is H), C$_1$–C$_{10}$ alkyl, aryl, C$_1$–C$_{10}$ alkoxy or siloxy groups of the formula:

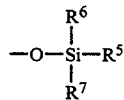

wherein R$^5$, R$^6$ and R$^7$, which may be the same or different, are selected from H, CH$_3$ or phenyl (provided that not more than one of R$^5$, R$^6$ and R$^7$ is H); and wherein R$^2$ may also be a group selected from siloxane oligomers or polymers of the structure:

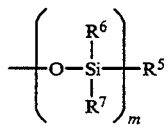

wherein R$^5$, R$^6$ and R$^7$ are defined as above and m is an integer from 2 to 100.

4. Monomers according to claim 2 wherein X is other than —CN and R is a C$_1$–C$_{12}$ hydrocarbyl group and R$^1$ is a C$_1$–C$_{10}$ hydrocarbyl, C$_6$–C$_{20}$ aryl or C$_6$–C$_{20}$ hydrocarbyl aryl group, or a substituted derivative thereof, further substituted with a Si or Ti containing group.

5. Monomers according to claim 4 wherein the Si containing group is of the formula:

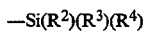

—Si(R$^2$)(R$^3$)(R$^4$)

wherein R$^2$, R$^3$ and R$^4$, which may be the same or different, are selected from H (provided that not more than one of R$^2$, R$^3$ and R$^4$ is H), C$_1$–C$_{10}$ alkyl, aryl, C$_1$–C$_{10}$ alkoxy or siloxy groups of the formula:

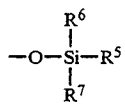

wherein $R^5$, $R^6$ and $R^7$, which may be the same or different, are selected from H, $CH_3$ or phenyl (provided that not more than one of $R^5$, $R^6$ and $R^7$ is H) wherein $R^2$ may also be a group selected from siloxane oligomers or polymers of the structure:

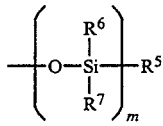

wherein $R^5$, $R^6$ and $R^7$ are defined as above and m is an integer from 2 to 100.

6. Monomers according to claim 5 wherein m is in the range from 2 to 5.

7. Monomers according to claim 5 wherein at least one of $R^2$, $R^3$ and $R^4$ is $C_1$-$C_5$ alkyl or phenyl.

8. Monomers according to claim 5 wherein Y is —$COO(CH_2)_n$—O—$Si(R^2)(R^3)(R^4)$ wherein $R^2$, $R^3$ and $R^4$ are as defined in claim 5 and n is an integer from 1 to 5.

9. Monomers according to claim 8 wherein $R^2$, $R^3$ and $R^4$ are $C_1$-$C_{10}$ alkyl land n is at least 3.

10. Anionically polymerizable monomers of the formula:

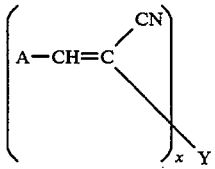

wherein A is —H or —CH=$CH_2$, Y is an x-valent strong electron withdrawing group containing at least one silicon or titanium atom and x is equal to 1.

11. Monomer according to claim 10 which is 3-trimethylsilylpropyl 2-cyanoacrylate.

12. Monomers according to claim 10 wherein Y is selected from —$COR^1$, —$COOR^1$, —$SO_2R^1$ or —$SO_3R^1$ wherein $R^1$ is a group containing Si or Ti.

13. Monomers according to claim 12 wherein $R^1$ is —$Si(R^2)(R^3)(R^4)$,
wherein $R^2$, $R^3$ and $R^4$, which may be the same or different, are selected from H (provided that not more than one of $R^2$, $R^3$ and $R^4$ is H), $C_1$-$C_{10}$ alkyl, aryl, $C_1$-$C_{10}$ alkoxy or siloxy groups of the formula:

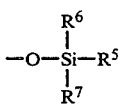

wherein $R^5$, $R^6$ and $R^7$, which may be the same or different, are selected from H, $CH_3$ or phenyl (provided that not more than one of $R^5$, $R^6$ and $R^7$ is H); and wherein $R^2$ may also be a group selected from siloxane oligomers or polymers of the structure:

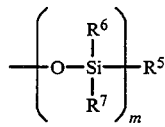

wherein $R^5$, $R^6$ and $R^7$ are defined as above and m is an integer from 2 to 100.

14. Monomers according to claim 12 wherein $R^1$ is a $C_1$-$C_{10}$ hydrocarbyl, $C_6$-$C_{20}$ aryl or $C_6$-$C_{20}$ hydrocarbyl aryl group, or a substituted derivative thereof, further substituted with a Si or Ti containing group.

15. Monomers according to claim 14 wherein the Si containing group is of the formula:
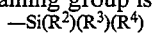
—$Si(R^2)(R^3)(R^4)$ wherein $R^2$, $R^3$ and $R^4$, which may be the same or different, are selected from H (provided that not more than one of $R^2$, $R^3$ and $R^4$ is H), $C_1$-$C_{10}$ alkyl, aryl, $C_1$-$C_{10}$ alkoxy or siloxy groups of the formula:

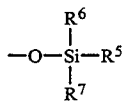

wherein $R^5$, $R^6$ and $R^7$, which may be the same or different, are selected from H, $CH_3$ or phenyl (provided that not more than one of $R^5$, $R^6$ and $R^7$ is H); and wherein $R^2$ may also be a group selected from siloxane oligomers or polymers of the structure:

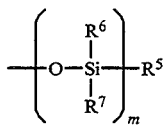

wherein $R^5$, $R^6$ and $R^7$ are defined as above and m is an integer from 2 to 100.

16. Monomers according to claim 15 wherein m is in the range from 2 to 5.

17. Monomers according to claim 15 wherein at least one of $R^2$, $R^3$ and $R^4$ is $C_1$-$C_5$ alkyl or phenyl.

18. Monomers according to claim 10 wherein Y is —$COO(CH_2)_n$—O—$Si(R^2)(R^3)(R^4)$ and wherein $R^2$, $R^3$ and $R^4$, which may be the same or different, are selected from H (provided that not more than one of $R^2$, $R^3$ and $R^4$ is H), $C_1C_{10}$ alkyl, aryl, $C_1$-$C_{10}$ alkoxy or siloxy groups of the formula:

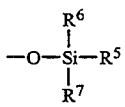

wherein $R^5$, $R^6$ and $R^7$, which may be the same or different, are selected from H, $CH_3$ or phenyl (provided that not more than one of $R^5$, $R^6$ and $R^7$ is H); and wherein $R^2$ may also be a group selected from siloxane oligomers or polymers of the structure:

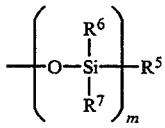

wherein $R^5$, $R^6$ and $R^7$ are defined as above and m is an integer from 2 to 100, and n is an integer of from 1 to 5.

19. Monomers according to claim 18 wherein m is in the range from 2 to 5.

20. Monomers according to claim 33 wherein $R^2$, $R^3$ and $R^4$ are $C_1$-$C_5$ alkyl and n is at least 3.

21. A silicon-containing α-cyanoacrylate represented by the formula:

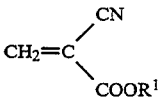

where $R^1$ is a $C_1$-$C_6$ alkyl group having at least one group of the formula:

thereon, and $R^2$, $R^3$ and $R^4$ are the same or different $C_1$-$C_{10}$ alkyl groups.

* * * * *